(12) United States Patent
Sadeghzadeh et al.

(10) Patent No.: US 11,839,743 B2
(45) Date of Patent: Dec. 12, 2023

(54) GRAPHIC USER INTERFACE FOR AUTOMATED INFUSATE DELIVERY

(71) Applicant: MEDTRONIC MINIMED, INC., Northridge, CA (US)

(72) Inventors: Mahta Sadeghzadeh, Los Angeles, CA (US); Salman Monirabbasi, Playa Vista, CA (US); Dmytro Y. Sokolovskyy, Moorpark, CA (US); Louis J. Lintereur, Stevenson Ranch, CA (US); Alexander S. Campbell, Encino, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 716 days.

(21) Appl. No.: 17/065,500

(22) Filed: Oct. 7, 2020

(65) Prior Publication Data

US 2022/0105268 A1    Apr. 7, 2022

(51) Int. Cl.
| | |
|---|---|
| *A61M 5/172* | (2006.01) |
| *G06F 3/04847* | (2022.01) |
| *G06T 11/00* | (2006.01) |
| *A61M 5/142* | (2006.01) |

(52) U.S. Cl.
CPC ....... *A61M 5/1723* (2013.01); *G06F 3/04847* (2013.01); *G06T 11/00* (2013.01); *A61M 5/14248* (2013.01); *A61M 2205/502* (2013.01); *A61M 2205/52* (2013.01); *A61M 2230/201* (2013.01)

(58) Field of Classification Search
CPC .......... A61M 5/1723; A61M 2205/502; A61M 2205/52; A61M 2230/201; A61M 2005/14208; A61M 2205/3569; A61M 5/168; A61M 5/172; A61M 2205/50; A61M 2230/20; A61M 5/14; A61M 5/142; G06F 3/04847; G06F 9/451; G06F 3/048; G06F 3/0484; G06F 9/44; G06F 9/06; G06T 11/00
See application file for complete search history.

(56) References Cited

U.S. PATENT DOCUMENTS

| | | |
|---|---|---|
| 4,562,751 A | 1/1986 | Nason et al. |
| 4,678,408 A | 7/1987 | Nason et al. |
| 4,685,903 A | 8/1987 | Cable et al. |
| 4,755,173 A | 7/1988 | Konopka et al. |
| 5,080,653 A | 1/1992 | Voss et al. |

(Continued)

*Primary Examiner* — Jason E Flick
(74) *Attorney, Agent, or Firm* — FORTEM IP (57) ABSTRACT

Methods, computer-readable medium, and devices that provide a graphic user interface for operating a medical infusion system are described. An exemplary method includes receiving analyte level information for a user; and providing a graphic user interface on a display element that includes an analyte level chart depicting analyte values and an infusate delivery chart. An exemplary chart depicts graphics showing basal amounts of infusate delivered by the system over time, wherein each graphic is illustrated with a dimension indicating an increased, same, or decreased amount relative to an immediately preceding graphic. Further, the exemplary chart depicts indicators showing bolus amounts delivered by the medical infusion system over time, wherein at least a portion of the bolus indicators is illustrated with a dimension not to scale.

20 Claims, 6 Drawing Sheets

(56) References Cited

U.S. PATENT DOCUMENTS

| | | |
|---|---|---|
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,892,085 B2 | 5/2005 | McIvor et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,674,288 B2 | 3/2014 | Hanson et al. |
| 2003/0114836 A1* | 6/2003 | Estes .............. A61M 5/172 604/890.1 |
| 2007/0123819 A1 | 5/2007 | Mernoe et al. |
| 2010/0049164 A1* | 2/2010 | Estes .............. A61M 5/1723 604/504 |
| 2010/0160861 A1 | 6/2010 | Causey, III et al. |
| 2010/0174229 A1* | 7/2010 | Hsu .............. A61M 5/142 340/5.82 |

\* cited by examiner

GRAPHIC USER INTERFACE FOR AUTOMATED INFUSATE DELIVERY

TECHNICAL FIELD

Embodiments of the subject matter described herein relate generally to medical devices, and more particularly, embodiments of the subject matter relate to fluid infusion devices such as personal insulin infusion pumps.

BACKGROUND

Portable medical devices are useful for patients that have conditions that must be monitored on a continuous or frequent basis. For example, diabetics are usually required to modify and monitor their daily lifestyle to keep their blood glucose (BG) in balance. The blood glucose level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels.

Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Such large amounts of data can be overwhelming to a patient or caregiver.

The use of automated insulin pumps relieve the patient of the need for syringes or drug pens and the administration of multiple, daily injections. Insulin pumps allow for the delivery of insulin in a manner that bears greater similarity to the naturally occurring physiological processes and can be controlled to follow standard or individually modified protocols to give the patient better glycemic control. However, automation of insulin delivery requires confidence by the patient that the delivery device is diagnosing BG levels and administering insulin properly.

Accordingly, it is desirable to provide methods, devices and computer-readable medium for use with a medical infusion system that provide a graphic user interface to communicate sufficient information to allay concern by a user that the medical infusion system is not functioning properly. Further, it is desirable for such methods, devices and computer-readable medium to allow for operation with the medical infusion system in a simple, safe, and reliable manner in a real world setting. Furthermore, other desirable features and characteristics will become apparent from the subsequent detailed description and the appended claims, taken in conjunction with the accompanying drawings and the foregoing technical field and background.

BRIEF SUMMARY

Computer-implemented methods, non-transitory computer-readable medium, and devices that provide a graphic user interface for operating a medical infusion system are described. An exemplary method includes receiving analyte level information for a user, wherein the analyte level information is associated with one or more analyte measurement times; and providing a graphic user interface on a display element that includes an analyte level chart and an infusate delivery chart. An exemplary analyte level chart depicts a series of analyte values included in the analyte level information. An exemplary infusate delivery chart depicts basal graphics showing basal amounts of infusate delivered by the medical infusion system over time, wherein each basal graphic is illustrated with a dimension indicating an increased amount, same amount or decreased amount relative to an immediately preceding basal graphic. Further, the exemplary infusate delivery chart depicts bolus indicators showing bolus amounts of the infusate delivered by the medical infusion system over time, wherein each bolus indicator has a dimension indicative of the respective bolus amount, and wherein the dimension of at least a portion of the bolus indicators is illustrated not to scale.

In exemplary embodiments, a computing device is provided for operating a medical infusion system. The computing device includes a display element, one or more processors, and memory storing computer-readable instructions that, when executed by the one or more processors, cause the computing device to perform actions. The actions include receiving glucose level information for a user, wherein the glucose level information is associated with one or more blood glucose measurement times. Further, the actions include providing a graphic user interface on the display element. An exemplary graphic user interface comprises a glucose level chart and an insulin delivery chart. An exemplary glucose level chart depicts a series of glucose values included in the glucose level information. An exemplary insulin delivery chart depicts basal graphics showing basal amounts of insulin delivered by the medical infusion system over time, wherein each basal graphic is illustrated with a dimension indicating an increased amount, same amount or decreased amount relative to an immediately preceding basal graphic. Further, an exemplary insulin delivery chart depicts bolus indicators showing bolus amounts delivered by the medical infusion system over time, wherein each bolus indicator is illustrated with a dimension, and wherein the dimension of at least one bolus indicator is not to scale.

An exemplary embodiment includes a non-transitory computer-readable medium including instructions that, when executed by at least one processor, cause performance of operations. The operations include communicating with a controller of a medical infusion system to cause the medical infusion system to dispense insulin to a user, receiving glucose level information for the user, wherein the glucose level information is associated with one or more glucose measurement times, and providing a graphic user interface on a display element. An exemplary graphic user interface includes a glucose level chart and an insulin delivery chart. An exemplary glucose level chart depicts a series of blood glucose values included in the glucose level information. An exemplary insulin delivery chart depicts basal graphics showing basal amounts of insulin delivered by the medical infusion system over time, wherein each basal graphic is illustrated with a dimension indicating an increased amount, same amount or decreased amount relative to an immediately preceding basal graphic. Further, an exemplary insulin delivery chart depicts bolus indicators showing bolus amounts delivered by the medical infusion system over time, wherein each bolus indicator is illustrated with a dimension, and wherein the dimension of at least one bolus indicator is not to scale.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, embodiments of a system or a component may employ various integrated circuit components, e.g., memory elements, digital signal processing elements, logic elements, look-up tables, or the like, which may carry out a variety of functions under the control of one or more microprocessors or other control devices.

Exemplary embodiments of the subject matter described herein are used in conjunction with medical devices, such as portable electronic medical devices. Although many different applications are possible, exemplary embodiments are used in applications that incorporate a fluid infusion device (or infusion pump) as part of an infusion system deployment.

For the sake of brevity, conventional techniques related to infusion system operation, insulin pump and/or infusion set operation, blood glucose sensing and monitoring, force sensors, signal processing, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,320; 6,558,351; 6,659,980; 6,752,787; 6,817,990; 6,932,584; and 7,621,893; which are herein incorporated by reference.

The subject matter described here relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infusate or infused fluid may be insulin (as used herein "insulin" includes insulin and synthetic-made insulins typically referred to as analogs of human insulin). In embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. Further, the analyte or sensed and measured constituent may be blood glucose, interstitial glucose or other selected analyte.

Figure 1:
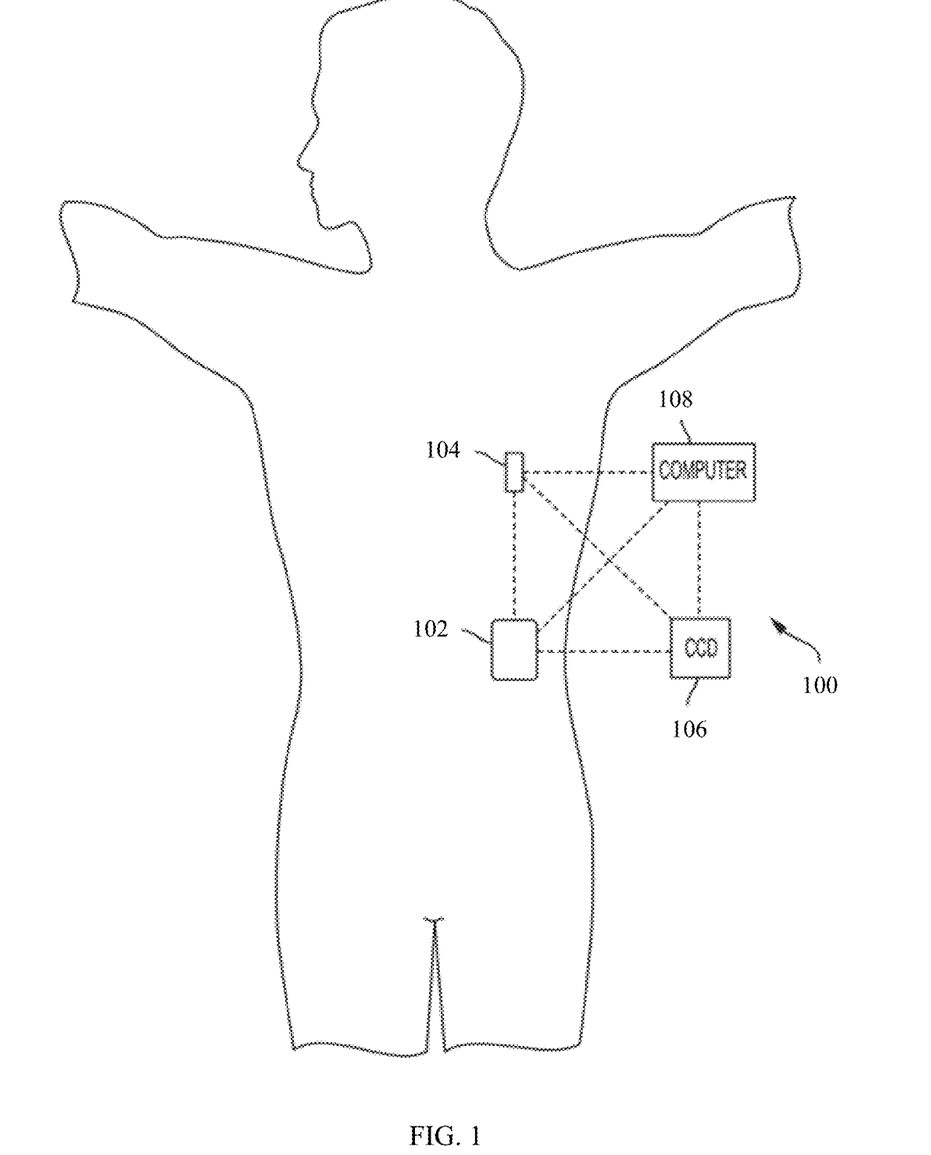
FIG. 1 depicts an exemplary embodiment of a medical infusion system.

Turning now to FIG. 1, an exemplary infusion system 100 includes, without limitation, a fluid infusion device (such as an injection pen, an infusion pump, patch pump or other suitable device) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. FIG. 1 illustrates that the infusion device 102 and the sensing arrangement 104 may be secured at desired locations on the body of a user (or patient), such as when the infusion device 102 is a patch pump. However, the infusion device 102 may be held in the hand of the user or patient, such as when the infusion device 102 is an injection pen or infusion pump. An exemplary infusion set associated with the infusion device 120 may or may not be secured to the body. For an embodiment as illustrated in FIG. 1, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, such as a liquid or gel, or an agent suspended in a fluid into the body of a user. An exemplary infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In exemplary embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as an analyte level, e.g., a glucose level such as a blood glucose level or a sensor glucose level, or the like, of the user, and provide data indicative of the analyte level to the infusion device 102, the CCD 106 and/or the computer 108. An exemplary sensing arrangement 104 may include a continuous glucose monitor and/or a blood glucose meter.

Further, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In exemplary embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, an exemplary sensing arrangement 104 may be secured to the body of the user or embedded in the body of the user at a location that is remote from the location of the infusion device 102. An exemplary sensing arrangement 104 may be incorporated within the infusion device 102. An exemplary sensing arrangement 104 may be separate and apart from the infusion device 102, and may be, for example, part of the CCD 106. The sensing arrangement 104 may be configured to receive a biological sample, analyte, or the like, to measure a condition of the user.

In exemplary embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. An exemplary infusion device 102 may include all control functions, and may operate without a separate CCD 106 and/or computer 108.

An exemplary CCD 106 may be a portable electronic device, such as a smart phone, a smart watch or other wearable device. In exemplary embodiments, the infusion device 102 and/or the sensing arrangement 104 may be configured to transmit data to the CCD 106 and/or the computer 108 for display or processing of the data by the CCD 106 and/or the computer 108.

In exemplary embodiments, the CCD 106 and/or the computer 108 may provide information to the user that facilitates the user's subsequent use of the infusion device 102. For example, the CCD 106 may provide information to the user to indicate the rate or dose of medication administered into the user's body. In exemplary embodiments, the CCD 106 may provide information to the infusion device 102 to autonomously control the rate or dose of medication administered into the body of the user. In exemplary embodiments, the sensing arrangement 104 may be integrated into the CCD 106 and may allow the user to monitor a condition by providing, for example, a sample of his or her blood to the sensing arrangement 104 to assess his or her condition. In exemplary embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In exemplary embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119, 028, 6,589,229, 6,740,072, 6,827,702, 7,323,142, and 7,402, 153 or U.S. patent application Ser. No. 13/966,120, all of which are incorporated herein by reference in their entirety. In such embodiments, the sensing arrangement 104 is configured to sense or measure a condition of the user, such as, glucose level, such as a blood glucose level or sensor glucose level, or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In exemplary embodiments, the sensing arrangement 104 and/or the infusion device 102 may be configured to utilize the closed-loop system only for a portion of the day, for example only when the user is asleep or awake. As described, the closed-loop system may be used to change basal delivery rates and/or update parameters, settings, and/or models for dosage delivery that are specific to the user.

As described, the infusion device 102, CCD 106 (such as a smart phone), and/or computer 108 can serve as the user interface of the infusion system 100. An exemplary user interface allows a user to see actionable data and to send commands. An exemplary user interface is provided on a separate CCD 106 and/or computer 108, and is not provided on the infusion device 102, thereby eliminating a need for a dedicated display and user input device. In exemplary embodiments, a dedicated display and user input device with reduced complexity is provided on infusion device 102. In this manner, costs and energy expenditure for infusion device 102 may be reduced.

Figure 2:
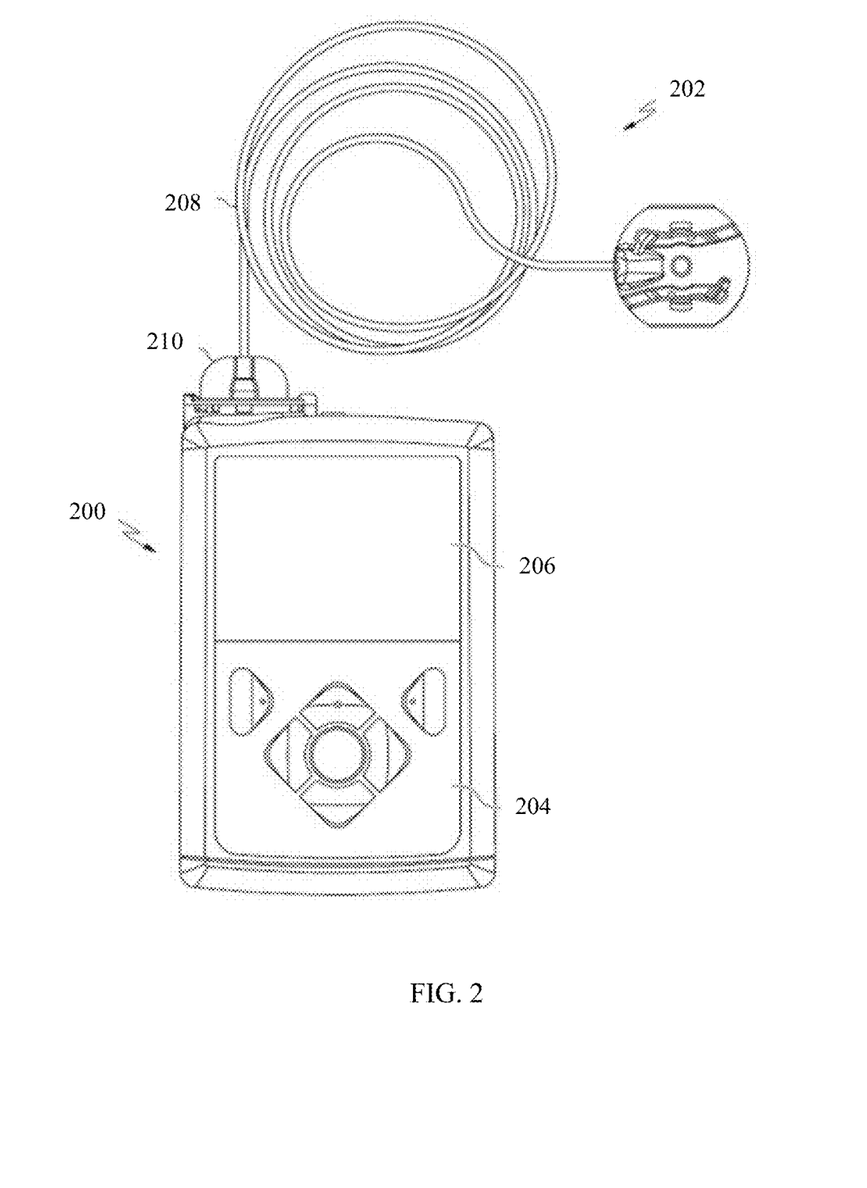
FIG. 2 depicts a plan view of an exemplary embodiment of a medical infusion device suitable for use in the system of FIG. 1.

FIG. 2 depicts an exemplary infusion pump or fluid infusion device 200 suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. FIG. 2 depicts only some aspects of the fluid infusion device 200 in a simplified manner and the fluid infusion device 200 includes additional elements, features, or components that are not shown or described in detail herein. As shown, an infusion set 202 is coupled to the fluid infusion device 200.

The exemplary fluid infusion device 200 shown in FIG. 1 includes a user interface 204 that includes several buttons that can be activated by the user. These buttons can be used to manually administer a bolus of insulin, to change therapy settings, to change user preferences, to select display features, and the like. Although not required, the illustrated embodiment of the fluid infusion device 200 includes a display element 206. The display element 206 can be used to present various types of information or data to the user, such as, without limitation: the current glucose level of the patient; the time; a graph or chart of the patient's glucose level versus time; device status indicators; etc. In exemplary embodiments, the display element 206 is realized as a touch screen display element.

The fluid infusion device 200 accommodates a fluid reservoir (hidden from view in FIG. 2) for the fluid to be delivered to the user. A length of tubing 208 is the flow path that couples the fluid reservoir to the infusion set 202. The tubing 208 extends from the fluid infusion device 200 to the infusion set 202, which provides a fluid pathway with the body of the user. A removable cap or fitting 210 is suitably sized and configured to accommodate replacement of fluid reservoirs (which are typically disposable) as needed. In this regard, the fitting 210 is designed to accommodate the fluid path from the fluid reservoir to the tubing 208.

Figure 3:
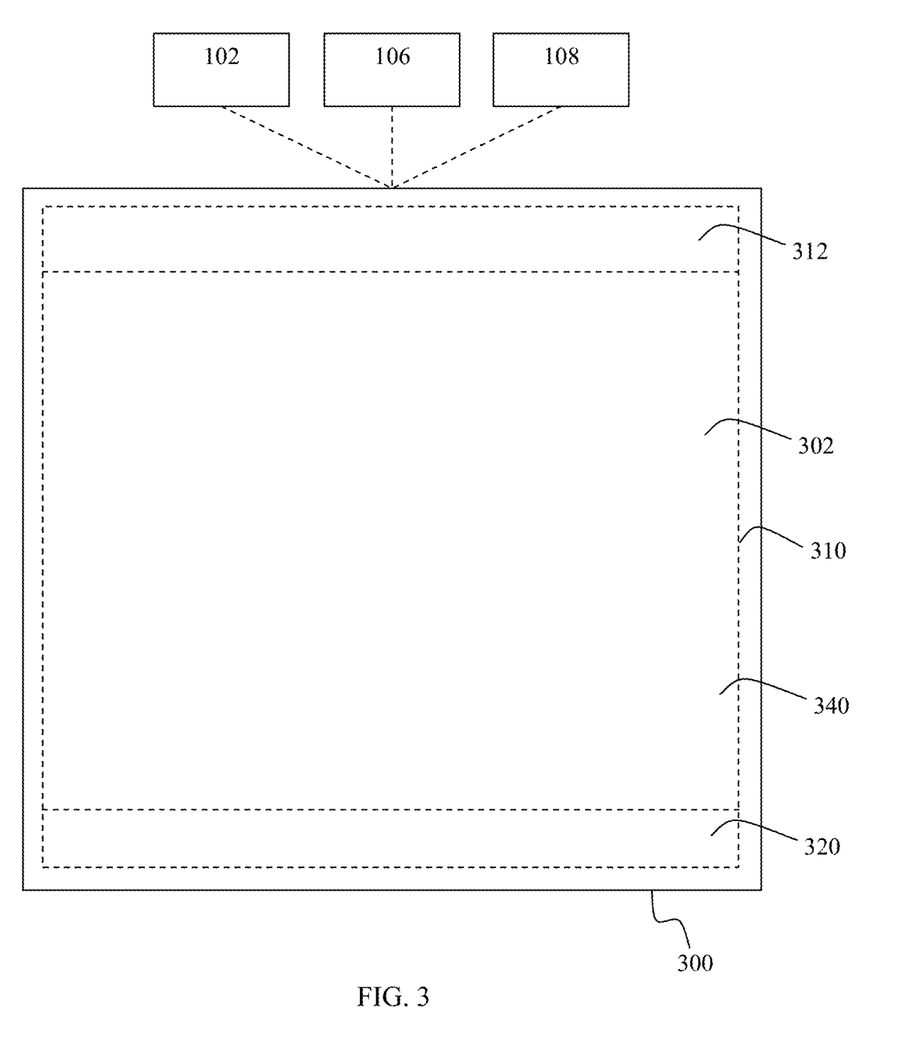
FIG. 3 is a schematic representation of embodiments of a system for displaying physiological patient data.

FIG. 3 is a schematic representation of embodiments of a display element 300 for displaying physiological patient data and operation data of the infusion system 100. As described above in FIG. 1, the display element 300 may be included in the infusion device 102, the CCD 106 and/or the computer 108, such as, for example, as display element 206 in the fluid infusion device 200 of FIG. 2.

As shown, display element 300 provides a graphic user interface 302 that includes selectable features that can be activated by the user, such as to manually administer a bolus of insulin, to change therapy settings, to change user preferences, to select display features, and the like. The display element 300 may present various types of information or data to the user, such as, without limitation: the current glucose level of the patient; the time; a graph or chart of the patient's glucose level versus time; device status indicators; etc.

In FIG. 3, the display element 300 includes a screen 310, such as a touch screen, that serves as the graphic user interface 302. The screen 310 may appear on the display element 300 on the infusion device 102 and/or computer 108 by default. The screen 310 may appear on a display element 300 on the CCD 106 when a user selects an icon for monitoring or operating the infusion system 100. If the user is already logged in, screen 310 can appear whenever the user selects an icon for an infusion system control application. If the user is not logged in, a log-in screen can appear for the user to enter secure identifying information (e.g., a user name and password, a thumb print, an iris scan, etc.). Moreover, as discussed below, the infusion system control application can also prompt a user to pair one or more insulin delivery devices, continuous glucose monitors, and/or blood glucose monitors during an initial log in and/or if CCD 106 fails to find a paired insulin delivery device, continuous glucose monitors, and/or blood glucose monitors.

Screen 310 can provide the user with a simplified view of the infusion system status to help the user quickly understand whether the infusion system is operating appropriately and promote routine activities, while also allowing the user to access additional data if the user is interested in more detailed system information. Display screen 310 may include a header area 312 that includes mobile and wife signal strength indicator, a CCD power display, a logo, a time display, and a user name. Header area 312 can provide the user with comfort about the system status of the infusion system 100 and assure the user that the component 106 or 108 (of FIG. 1) is their personal component. In an exemplary display screen 310, header area 312 is not expressly delineated.

In exemplary embodiments, display screen 310 may be a home screen and may include a selectable graphic button 320 to proceed to the graphic user interface 302. In exemplary embodiments, a portion 340 of the display screen 310 may include the graphic user interface 302 as shown in FIG. 3.

Figure 4:
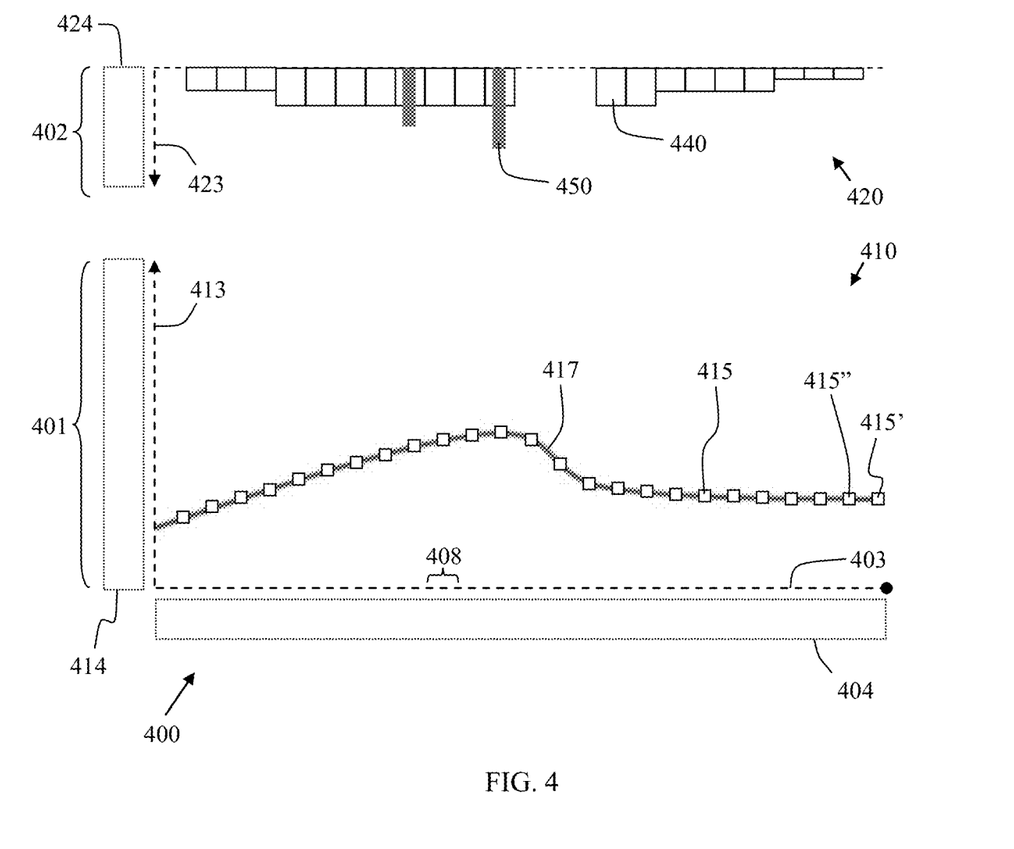
FIG. 4 is a face view of embodiments of an infusate delivery graphic user interface displaying physiological patient data.

Referring now to FIG. 4, a schematic representation of embodiments of a graphic user interface 400 is provided. As explained in reference to FIG. 3, the graphic user interface 400 may be included in the display screen 310 of the display element 300 as the graphic user interface 302, or may be a separate graphic user interface 302 navigable from the display screen 310.

As shown in FIG. 4, the graphic user interface 400 includes a first region 401 and a second region 402. In the first region 401, the graphic user interface 400 includes an analyte level or glucose level chart 410. In the second region 402, the graphic user interface 400 provides an infusate delivery or insulin delivery chart 420. Both charts 410 and 420 share an x-axis 403 that depicts time. In exemplary embodiments, the x-axis 403 need not be expressly depicted by the graphic user interface 400. In the direction of the x-axis 403, chart 410 may include an x-axis label 404 in which numbers and time units are provided.

In exemplary embodiments, data associated with the current time is provided at the rightmost edge of charts 410 and 420. As time passes, older data points move to the left of charts 410 and 420 and is replaced by more recent data points. An exemplary graphic user interface 400 provides for each discrete time of measurement to have a selected number of pixels in the direction of the x-axis, i.e., a width 408. An exemplary graphic user interface 400 includes an interactive control that allows the user to select an amount of time represented by the time axis 403. For example, the time axis 403 may be selected and various time frames, such as one week, five days, three days, one day, or other desirable time period may be selected. Accordingly, the widths 408 of the discrete time measurements may be increased or decreased as desired.

Analyte or Glucose Level Chart

An exemplary analyte level chart 410 depicts a series of analyte values included in the analyte level information received from the sensing arrangement 104 of the system 100 through the use of graphic features 415. The graphic features 415 representing analyte values in the analyte level chart 410 are aligned over the time axis 403 to reflect the times that the analyte values were measured.

Analyte level chart 410 includes a y-axis 413 perpendicular to the time axis 403. In exemplary embodiments, the y-axis 413 need not be expressly depicted by the graphic user interface 400. In the direction of the y-axis 413, chart 410 may include a y-axis label 414 in which numbers are provided for glucose measurements. For example, glucose measurements may be provided in milligrams per deciliter (mg/dL) or in millimoles per liter (mmol/L). The y-axis label 414, or another feature of the system 100, may be selectable by the user to convert between milligrams per deciliter and millimoles per liter or other desired units.

As shown, the graphic features 415 of the exemplary glucose level chart 410 represent analyte values or measurements at the associated time of the time axis 403, such as a dot, mark or desired suitable shape that may be displayed graphically. A most recent analyte value is indicated by graphic feature 415' at a rightmost position while an immediately preceding analyte value is indicated by graphic feature 415" at the position immediately to the left. As shown, a line or slope 417 may be presented as interconnecting each graphic feature 415. In exemplary embodiments, the graphic features 415 need not be distinguishable from the line 417, e.g., the graphic features 415 may be dots that form the line 417. In other words, the line 417 may be shown alone without any graphic features 415 that form the basis for the line 417. Graphic features 415 may be selectable such that the user clicks on a selected graphic feature to open a sub-window or new window in which the specific analyte measurement value is displayed to a desired specificity, i.e., tenths, hundredths, etc., as well as the time when the analyte measurement was taken, an identification of the glucose measurement device, and/or the units for the measurement. For example, the analyte measurement value may be a glucose measurement value from a continuous glucose monitor (CGM) or blood glucose meter (BGM).

Infusate or Insulin Delivery Chart

In FIG. 4, the exemplary infusate delivery chart 420 includes depictions such as basal graphics 440 showing basal amounts of infusate delivered by the system 100 and bolus indicators 450 showing bolus amounts of the infusate delivered by the system 100. It is noted that a bolus amount may be delivered as a correction bolus, may be delivered to compensate for an unannounced meal, or may be delivered under other circumstances. Further, a bolus amount may be delivered automatically or manually. In an exemplary embodiment, the bolus amounts are automatically delivered bolus amounts, and while not shown, the infusate delivery chart 420 may also include depictions for manually administered bolus amounts of infusate delivered by command of the user. As shown, the basal graphics 440 are aligned over the time axis 403 to reflect the times that the basal amounts were administered. Further, the bolus indicators 450 are aligned over the time axis 403 to reflect the times that the bolus amounts were delivered. In the illustrated embodiment, the exemplary bolus indicators 450 are located directly overlying the basal graphics 440 corresponding to a same time period.

Infusate delivery chart 420 includes a y-axis 423 perpendicular to the time axis 403 and collinear with the y-axis 413 of the analyte level chart 410. In exemplary embodiments, the y-axis 423 need not be expressly depicted by the graphic user interface 400. In the direction of the y-axis 423, chart 420 may include a y-axis label 424 in which an infusate and/or units are identified. In exemplary charts 420, no numbers are provided to identify the amount of infusate indicated by the chart 420. Further, in the direction of the y-axis 423, chart 420 or portions thereof may not be to scale and may not be labeled. Therefore, absolute amounts of infusate delivered as basal amounts, as automatic bolus amounts, or optionally as manually commanded bolus amounts, are not understandable from the chart 420. Rather, only relative amounts of infusate delivered as basal amounts, as bolus amounts, whether automatically or manually commanded bolus amounts, may be determined from the chart 420 based on comparisons of previous basal graphics 440 and/or bolus indicators 450.

Figure 5:
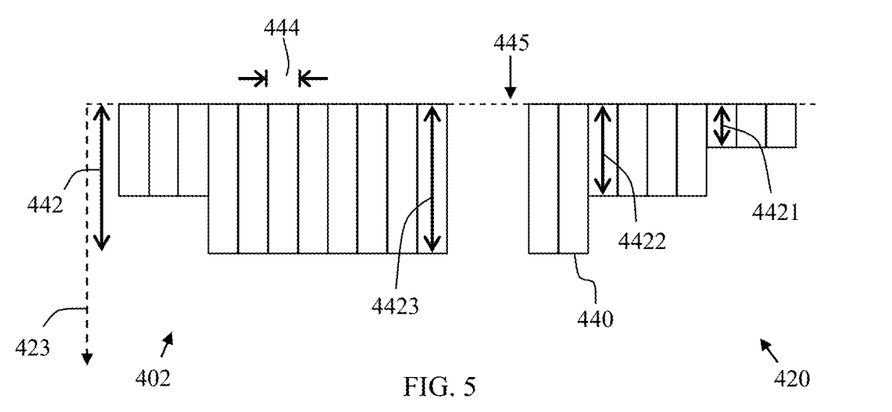
FIG. 5 is an enlarged view of the infusate chart of the graphic user interface of FIG. 4, showing only the basal graphics for clarity of discussion.
Figure 6:
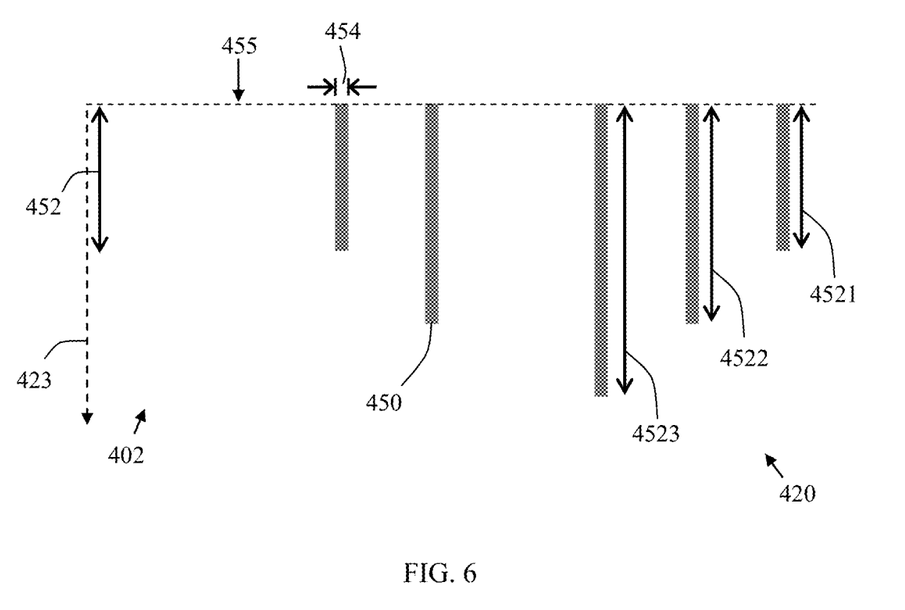
FIG. 6 is an enlarged view of the infusate chart of the graphic user interface of FIG. 4, showing only the bolus indicators for clarity of discussion.

While the terms "graphic features", "basal graphics", and "bolus indicators" are used to identify the elements representing analyte values, basal amounts and bolus amounts, and corresponding graphic depictions are used to represent analyte values, basal amounts and bolus amounts in FIG. 4 and the following FIGS. 5-6, these terms and depictions need not be interpreted distinctly. Rather, such terms are used for clarity and for facilitating antecedent bases. For example, a "graphic feature" and a "basal graphic" may be identical square dots of four pixels, or any other same shape of the same size. In exemplary embodiments in which bolus indicators are overlying basal graphics, there may necessarily be some optical distinction between the bolus indicators and basal graphics, such as a color or shade difference, shape difference, or the like.

FIG. 5 provides an enlarged view of the infusate delivery chart 420 of FIG. 4, showing only the basal graphics 440 for purposes of clarity and discussion. As shown in FIG. 5, each basal graphic 440 is illustrated with a dimension 442, such as a height or length in the y-axis direction, indicating an increased, same, or decreased amount relative to an immediately preceding basal graphic (the graphic to the immediate left of the selected graphic). In exemplary embodiments, the minimum basal amount is zero such that no basal amount is administered at a measurement time. As shown in FIG. 5, no basal graphic 440, i.e., a basal graphic with a dimension of zero, is depicted at that measurement time, such as at location 445. If a small, non-zero basal amount is administered at a measurement time, then the corresponding basal graphic 440 has a small dimension 4421. If an intermediate basal amount is administered at a measurement time, then the corresponding basal graphic 440 has an intermediate dimension 4422. If a maximum basal amount is administered at a measurement time, then the corresponding basal graphic 440 has a maximum dimension 4423. Thus, each basal amount that is administered is classified as either a minimum, small, intermediate, or maximum amount. It may be desirable to provide more than four possible dimensions 442. However, providing fewer possible dimensions 442 has been found to foster confidence in the automated performance of the system 100 without instigating manual interference in the administration of insulin. The basal graphics 440 may be provided with six, five, or four dimensions, i.e., zero, small, medium, and large, or with other suitable dimensions.

Further, exemplary basal graphics 440 are not selectable or queryable for additional information or data. In other words, in an exemplary graphic user interface 400, the user cannot receive any further information about a basal graphic 440 beyond the time the basal amount was administered (based on the time axis 403) and the relative size of the basal amount, as indicated by a zero dimension, the small dimension 4421, intermediate dimension 4422, or maximum dimension 4423. Thus, the graphic user interface 400 prohibits viewing numerical values of basal amounts by the user.

Cross-referencing FIGS. 4 and 5, it may be seen that exemplary basal graphics 440 are formed with a dimension in the x-axis direction, i.e., a width 444 that is equal to the dedicated width 408 of each time period. Thus, adjacent basal graphics 440 contact one another to provide a solid band of basal graphics. As a result, a step is formed when two basal graphics 440 having different height or length dimensions are adjacent one another.

FIG. 6 provides an enlarged view of the infusate delivery chart 420 of FIG. 4, showing only the bolus indicators 450 for purposes of clarity and discussion. As shown in FIG. 6, each bolus indicator 450 is illustrated with a dimension 452, such as a height or length in the y-axis direction, indicating an increased, same, or decreased amount relative to a preceding bolus indicator 450. If no bolus amount is administered at a measurement time, then no bolus indicator 450 is depicted at that measurement time, such as at location 455. If a minimum bolus amount is administered at a measurement time, then the corresponding bolus indicator 450 has a minimum dimension 4521. If an intermediate bolus amount is administered at a measurement time, then the corresponding bolus indicator 450 has an intermediate dimension 4522. If a maximum bolus amount is administered at a measurement time, then the corresponding bolus indicator 450 has a maximum dimension 4523. Thus, each bolus amount that is administered is classified as either a minimum, intermediate, or maximum amount. It may be desirable to provide more than three possible dimensions 452. However, providing fewer possible dimensions 452 has been found to foster confidence in the automated performance of the system 100 without instigating manual interference in the administration of insulin. The bolus indicators 450 may be provided with six, five, four, or three dimensions, or with other suitable dimensions.

In exemplary embodiments, the minimum bolus amount is equal to the maximum basal amount. Cross-referencing FIGS. 5 and 6, the minimum dimension 4521 of the bolus indicator 450 is equal to the maximum dimension 4423 of the basal graphic 440. At the minimum dimension 4521, an exemplary bolus indicator 450 is illustrated to scale with respect to the minimum bolus amount delivered.

Further, at least a portion of the exemplary bolus indicators 450 are not illustrated to scale with respect to the bolus amounts delivered. For example, at the maximum dimension 4523, the exemplary bolus indicator 450 may not be illustrated to scale with respect to the bolus amount delivered. Specifically, for an exemplary graphic user interface 400, the maximum dimension 4523 of the bolus indicator 450 is capped such that high bolus amounts are not graphically indicated by the bolus indicator 450. In FIG. 6, the maximum dimension 4523 of the bolus indicator 450 is about double the minimum dimension 4521 of the bolus indicator 450. However, the actual amount of a selected bolus amount may be greater than double the minimum bolus amount. Depicting the bolus indicators 450 with a capped maximum value may be helpful in not alarming a user by the actual bolus amount administered, when such amounts are higher than typical.

Therefore, a portion of the bolus indicators 450, such as those having a minimum dimension 4521 may be proportional to the bolus amount at a selected scale. Further, a portion of the bolus indicators 450, such as those having an intermediate dimension 4522 may be proportional to the bolus amount at the same selected scale. Even a portion of the bolus indicators 450 having a maximum dimension 4523 may be proportional to the bolus amount at the same selected scale. (For example, bolus indicators 450 representing a bolus amount that is exactly double the minimum bolus amount). However, a portion of the bolus indicators 450 having a maximum dimension 4523 may be not be proportional to the bolus amount at the same selected scale, i.e., not to scale. (For example, bolus indicators 450 representing a bolus amount that is more than double the minimum bolus amount). While the specific ratio of double the minimum dimension is described here, any desired ratio may be employed for capping the maximum dimension.

Unlike the exemplary basal graphics 440, the exemplary bolus indicators 450 may be selected and/or otherwise queried for additional information or data. Specifically, an exemplary graphic user interface 400 includes an interactive control that allows the user to view a numerical value of a selected bolus amount. For example, the user may click or otherwise query a selected bolus indicator 450 to open a sub-window or new window in which the specific bolus amount value is displayed to a desired specificity, i.e., tenths, hundredths, etc., as well as the time when the bolus amount was administered, and the units for the bolus amount value.

Cross-referencing FIGS. 4 and 6, it may be seen that exemplary bolus indicators 450 are formed with a dimension in the x-axis direction, i.e., a width 454, that is narrower than the dedicated width 408 of each time period. Thus, adjacent bolus indicators 450 appear as distinct, non-connected, shapes.

Figure 7:
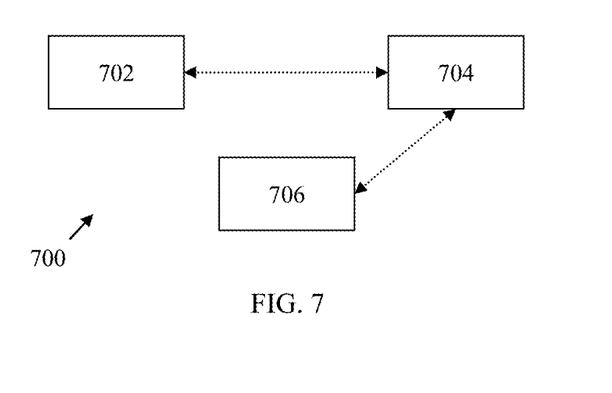
FIG. 7 is a schematic depicting a computing device for operating a medical infusion system according to embodiments.

Referring to FIG. 7, a computing device 700 for operating a medical infusion system is illustrated. An exemplary computing device 700 includes a display element 702, one or more processors 704, and memory storing computer-readable instructions 706 that, when executed by the one or more processors, cause the computing device to communicate with a controller of a medical infusion system to cause the medical infusion system to dispense insulin to a user, receive glucose level information for the user, wherein the glucose level information is associated with one or more blood glucose measurement times; and provide a graphic user interface on the display element. The graphic user interface comprises (a) a glucose level chart depicting a series of blood glucose values included in the glucose level information and (b) an insulin delivery chart. The insulin delivery chart depicts basal graphics showing basal amounts of insulin delivered by the medical infusion system over time, wherein each basal graphic is illustrated with a dimension indicating an increased amount, same amount or decreased amount relative to an immediately preceding basal graphic; and bolus indicators showing bolus amounts delivered by the medical infusion system over time, wherein at least a portion of the bolus indicators is illustrated with a dimension not to scale.

As described above, the display element 702 may be provided on an infusion device, such as infusion device 102 of FIG. 1, a CCD like a smart phone or other mobile device, such as CCD of 106 of FIG. 1, and/or a computer, such as computer 108 of FIG. 1. Also, the processors 704 may be included in an infusion device, such as infusion device 102 of FIG. 1, a CCD like a smart phone or other mobile device, such as CCD of 106 of FIG. 1, and/or a computer, such as computer 108 of FIG. 1. Further, the memory storing computer-readable instructions 706 may be stored on an infusion device, such as infusion device 102 of FIG. 1, a CCD like a smart phone or other mobile device, such as CCD of 106 of FIG. 1, and/or a computer, such as computer 108 of FIG. 1.

Figure 8:
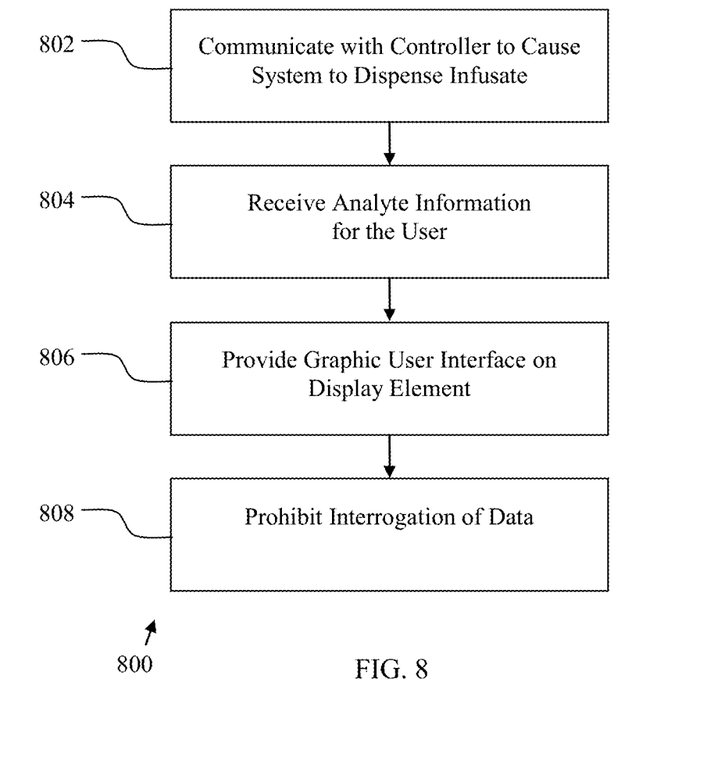
FIG. 8 depicts a method according to embodiments herein.

FIG. 8 depicts a method 800. As shown, the method 800 includes communicating with a controller of a medical infusion system to cause the medical infusion system to dispense an infusate to a user at action block 802. Further, the method includes receiving analyte level information for the user, wherein the analyte level information is associated with one or more analyte measurement times, at action block 804. Also, the method 800 includes providing a graphic user interface on a display element at action block 806. As described above, the graphic user interface includes (a) an analyte level chart depicting a series of analyte values included in the analyte level information and (b) an infusate delivery chart. Further, the infusate delivery chart depicts basal graphics and bolus indicators as described above.

The method 800 may further include prohibiting interrogation of data such that a user cannot mathematically determine how much infusate has been delivered by the infusion system at action block 808. For example, the method may include prohibiting display of the actual basal amounts of infusate delivered.

For the sake of brevity, conventional techniques related to glucose sensing and/or monitoring, computing including image capture and comparison and other functional aspects of the subject matter may not be described in detail herein. In addition, certain terminology may also be used in the herein for the purpose of reference only, and thus is not intended to be limiting.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A computer-implemented method for a medical infusion system, comprising:
   receiving analyte level information for a user, wherein the analyte level information is associated with one or more analyte measurement times; and
   providing a graphic user interface on a display element that includes an analyte level chart and an infusate delivery chart, wherein the analyte level chart depicts a series of analyte values included in the analyte level information, and wherein the infusate delivery chart depicts:
   basal graphics showing basal amounts of infusate delivered by the medical infusion system over time, wherein each basal graphic is illustrated with a dimension indicating an increased amount, same amount or decreased amount relative to an immediately preceding basal graphic; and
   bolus indicators showing bolus amounts of the infusate delivered by the medical infusion system over time, wherein each bolus indicator has a dimension indicative of the respective bolus amount, and wherein the dimension of at least a portion of the bolus indicators is illustrated not to scale.

2. The method of claim 1 wherein the infusate is insulin and wherein the analyte level information is glucose level information.

3. The method of claim 1 wherein at least a portion of the bolus indicators are not illustrated to scale with respect to the bolus amounts delivered.

4. The method of claim 1 wherein the bolus indicators are located overlying the basal graphics.

5. The method of claim 1 wherein:
   the basal graphics have a selected maximum dimension indicative of a maximum basal amount of infusate;
   the bolus indicators have a minimum dimension substantially equal to the selected maximum dimension of the basal graphics;
   at the minimum dimension, the bolus indicators are illustrated to scale with respect to a minimum bolus amount delivered;
   the bolus indicators have a maximum dimension; and
   at the maximum dimension, the bolus indicators are not illustrated to scale with respect to a maximum bolus amount delivered.

6. The method of claim 1 wherein the graphic user interface further comprises an interactive control that allows the user to view a numerical value of a selected bolus amount, and wherein the graphic user interface prohibits viewing numerical values of basal amounts by the user.

7. The method of claim 1 wherein:
   the analyte values of the analyte level chart are aligned over a time axis to reflect times that the analyte values were measured;
   the basal graphics are aligned over the time axis to reflect times that the basal amounts of infusate were administered; and
   the bolus indicators are aligned over the time axis to reflect the times that the bolus amounts were delivered.

8. The method of claim 7 wherein the graphic user interface further comprises an interactive control that allows the user to select an amount of time represented by the time axis.

9. The method of claim 7 wherein the time axis is the x-axis, and wherein the dimension of each basal graphic and the dimension of each bolus indicator extend in the direction of the y-axis.

10. The method of claim 1 wherein the analyte level information comprises glucose level information measured by a continuous glucose monitor and/or by a blood glucose meter.

11. A computing device for operating a medical infusion system, the computing device comprising:
   a display element;
   one or more processors; and
   memory storing computer-readable instructions that, when executed by the one or more processors, cause the computing device to perform actions comprising:
   receiving glucose level information for a user, wherein the glucose level information is associated with one or more blood glucose measurement times; and
   providing on the display element a graphic user interface including a glucose level chart and an insulin delivery chart, wherein the glucose level chart depicts a series of blood glucose values included in the glucose level information, and wherein the insulin delivery chart depicts:

basal graphics showing basal amounts of insulin delivered by the medical infusion system over time, wherein each basal graphic is illustrated with a dimension indicating an increased amount, same amount or decreased amount relative to an immediately preceding basal graphic; and bolus indicators showing bolus amounts delivered by the medical infusion system over time, wherein each bolus indicator is illustrated with a dimension, and wherein the dimension of at least one bolus indicator is not to scale.

12. The computing device of claim 11, wherein at least a portion of the bolus indicators are not illustrated to scale with respect to the bolus amounts delivered.

13. The computing device of claim 11 wherein:

the basal graphics have a selected maximum dimension indicative of a maximum basal amount of insulin;

the bolus indicators have a minimum dimension substantially equal to the selected maximum dimension of the basal graphics;

at the minimum dimension, the bolus indicators are illustrated to scale with respect to a minimum bolus amount delivered;

the bolus indicators have a maximum dimension; and at the maximum dimension, the bolus indicators are not illustrated to scale with respect to a maximum bolus amount delivered.

14. The computing device of claim 11 wherein:

at a minimum dimension, the bolus indicators are illustrated to scale with respect to a minimum bolus amount delivered; and at a maximum dimension; the bolus indicators are not illustrated to scale with respect to a maximum bolus amount delivered.

15. The computing device of claim 11 wherein the bolus indicators are located overlying the basal graphics.

16. The computing device of claim 11 wherein the graphic user interface further comprises an interactive control that allows the user to view a numerical value of a selected bolus amount, and wherein the graphic user interface is configured to prohibit viewing numerical values of basal amounts by the user.

17. The computing device of claim 11 wherein:

the blood glucose values of the glucose level chart are aligned over a time axis to reflect times that the blood glucose values were measured;

the basal graphics are aligned over the time axis to reflect times that the basal amounts were administered; and the bolus indicators are aligned over the time axis to reflect times that the bolus amounts were delivered.

18. The computing device of claim 17 wherein the graphic user interface further comprises an interactive control that allows the user to select an amount of time represented by the time axis.

19. The computing device of claim 17 wherein the time axis is the x-axis, and wherein the dimension of each basal graphic and the dimension of each bolus indicator extend in the direction of the y-axis.

20. A non-transitory computer-readable medium including instructions that, when executed by at least one processor, cause performance of operations that comprise:

communicating with a controller of a medical infusion system to cause the medical infusion system to dispense insulin to a user;

receiving glucose level information for the user, wherein the glucose level information is associated with one or more blood glucose measurement times; and providing a graphic user interface on a display element;

wherein the graphic user interface comprises a glucose level chart and an insulin delivery chart, wherein the glucose level chart depicts a series of blood glucose values included in the glucose level information, and wherein the insulin delivery chart depicts:

basal graphics showing basal amounts of insulin delivered by the medical infusion system over time, wherein each basal graphic is illustrated with a dimension indicating an increased amount, same amount or decreased amount relative to an immediately preceding basal graphic; and bolus indicators showing bolus amounts delivered by the medical infusion system over time, wherein each bolus indicator is illustrated with a dimension, and wherein the dimension of at least one bolus indicator is not to scale.

* * * * *